(12) United States Patent
Evans et al.

(10) Patent No.: US 6,376,731 B1
(45) Date of Patent: Apr. 23, 2002

(54) SELECTIVE OLEFIN OLIGOMERIZATION

(75) Inventors: Thomas I. Evans, Glenmoore;
Lawrence J. Karas, West Chester;
Ramesh Rameswaran, Exton, all of PA (US)

(73) Assignee: Arco Chemical Technology, l.p., Greenville, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,531

(22) Filed: Jan. 14, 2000

(51) Int. Cl.$^7$ .............................. C07C 2/74; C07C 2/08
(52) U.S. Cl. ............ 585/510; 585/515; 585/520; 585/521; 585/526; 585/255; 585/310; 585/316
(58) Field of Search ................................ 585/510, 515, 585/520, 521, 526, 255, 310, 316

(56) References Cited

U.S. PATENT DOCUMENTS

| | | | |
|---|---|---|---|
| 3,760,026 A | 9/1973 | Reusser et al. | 585/316 |
| 4,100,220 A | 7/1978 | Bowman et al. | 585/515 |
| 4,165,343 A | 8/1979 | Levine et al. | 585/638 |
| 4,197,185 A | 4/1980 | Le Page et al. | 208/71 |
| 4,447,668 A | 5/1984 | Smith, Jr. et al. | 585/634 |
| 5,847,252 A | 12/1998 | Stine et al. | 585/330 |
| 5,877,372 A | 3/1999 | Evans et al. | 585/510 |

*Primary Examiner*—Thuan D. Dang
(74) *Attorney, Agent, or Firm*—William C. Long

(57) ABSTRACT

A process is provided for the production of a gasoline blending fraction rich in isooctane by the dimerization of isobutylene using tertiary butyl alcohol modifier and lower alkane diluent; advantageously the isobutylene is derived from the dehydration of tertiary butyl alcohol.

3 Claims, 1 Drawing Sheet

SELECTIVE OLEFIN OLIGOMERIZATION

BACKGROUND OF THE INVENTION

1. Field of the Invention

The present invention relates to a process for the selective dimerization of isobutylene and especially to the use of $C_3$ and/or $C_4$ alkane as dimerization solvent together with the provision of tertiary butanol as a selectivity enhancing modifier during the dimerization.

2. Description of the Prior Art

The oligomerization of olefins such as isobutylene using acidic catalysts is a known reaction.

As described in U.S. Pat No. 3,760,026, a number of catalysts are known for this reaction including cold sulfuric acid, phosphoric acid on Kieselguhr, silica/alumina sometimes promoted with Ni, Co, Fe, Pt or Pd; activated natural clays plus activating substances such as ZnO metallic phosphates such as those of iron (III) and cerium optionally supported on carriers such as activated carbon, bauxite, activated carbon alone and with metal haliders such as $TiCl_2$ heteropolyacids such as silicotungstic acid on silica gel and phosphomolybdic acid; $BF_3H_3PO_4$ and $BF_3HPO_3$; dihydroxyfluroboric acid HF and fluorides or oxyfluorides of S, Se, N, P, Mo, Te, W, V and Si boiling below 300° C.; $BF_3$ dimethyl ether complexes; $BF_3$ hydrocarbon complexes; $BF_3 SO_2$; and $AlCl_3$ with cocatalysts such as dimethyl ether, HCl, and nitromethane. These catalysts and dimerization processes, including operating conditions, are known in the art.

An especially preferred catalyst is a sulfonic acid-type ion exchange resin such as Amberlyst A-15. U.S. Pat. No. 4,447,668 describes isobutylene dimerization using A-15 with methyl t-butyl ether as solvent.

Our U.S. Pat. No. 5,877,372 describes the selective dimerization of isobutylene using a sulfonic acid resin catalyst, tertiary butanol selectivity enhancing modifier and isooctane diluent.

U.S. Pat. No. 4,100,220 describes isobutylene dimerization using a sulfonic acid resin catalyst and tertiary butanol selectivity enhancing modifier. Minor amounts of butanes are shown in the dimerization feed.

Considerations associated with the isobutylene dimerization involve removal of the substantial heat of reaction and the requirement that high selectivity to the dimer product be maintained. The instant invention provides a process wherein these objectives are achieved.

SUMMARY OF THE INVENTION

In accordance with the present invention, a process is provided for the dimerization of isobutylene in the presence of both a selectivity enhancing amount of tertiary butanol and in the presence of $C_3$ and/or $C_4$, preferably $C_4$ alkane as diluent. In an especially preferred practice, tertiary butanol such as that derived from the Oxirane propylene oxide/tertiary butanol process is used as starting material and isooctane formed by hydrogenation of dimer is the ultimate product.

BRIEF DESCRIPTION OF THE DRAWING

The accompanying drawing is a schematic representation of an especially preferred practice of the invention.

DETAILED DESCRIPTION

Figure 1:
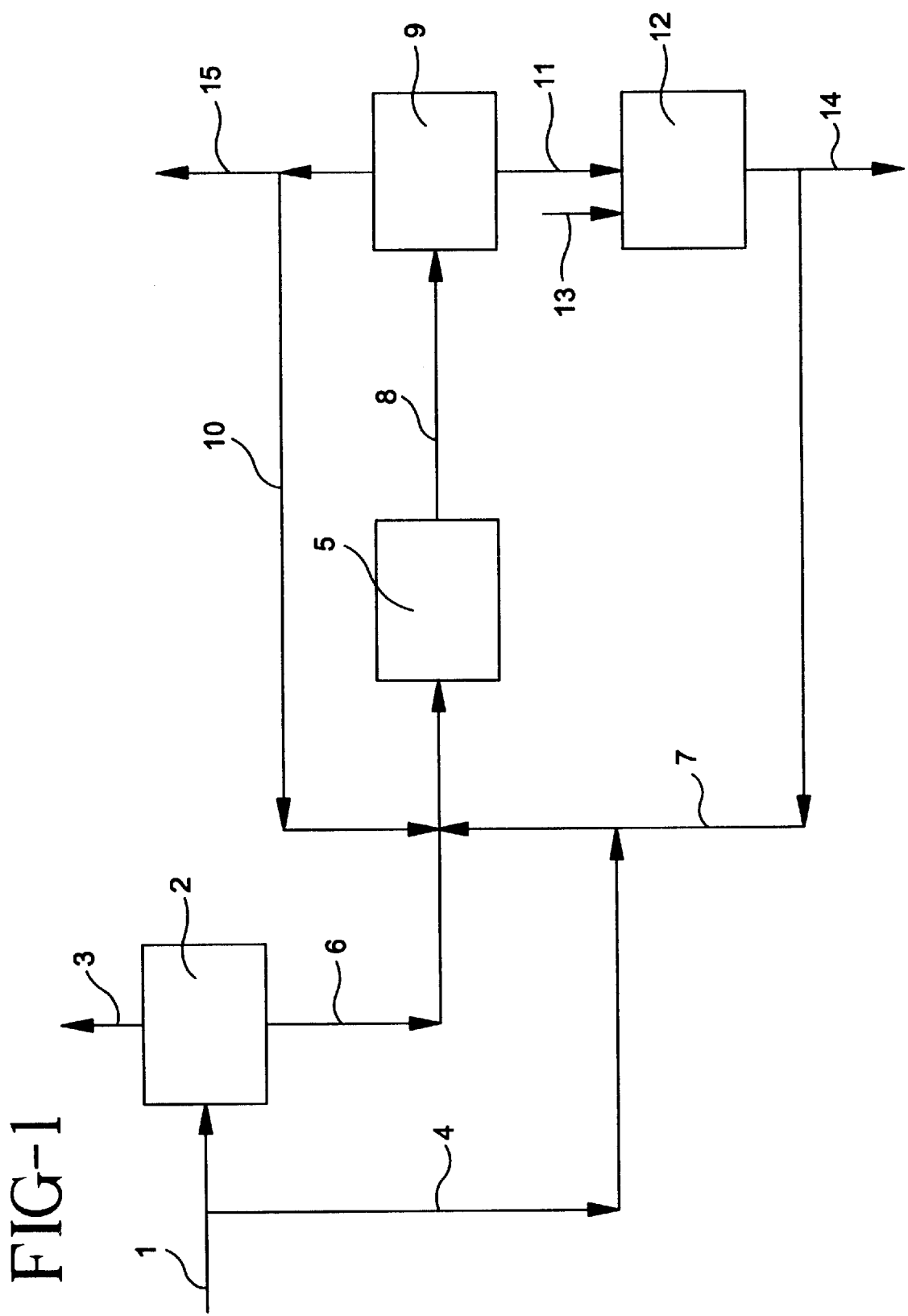

With reference to the drawing and the process represented therein, the tertiary butanol product from the Oxirane process forms the process starting material. The tertiary butanol is fed via line 1 to dehydration zone 2 wherein the tertiary butanol is dehydrated in accordance with known procedures to form isobutylene, water being removed from zone 2 via line 3.

A portion of the tertiary butanol is directed via line 4 for use as a selectivity enhancing modifier in the dimerization of isobutylene which takes place in zone 5 as will be hereinafter described.

Product isobutylene is removed from zone 2 via line 6 and passes to dimerization zone 5 wherein the isobutylene is dimerized in high selectivity to diisobutylene. In order to achieve high dimerization selectivity in zone 5, the provision both of tertiary butanol via lines 4 and 10 in selectivity enhancing amount and of butane via line 10 as dimerization diluent are important in carrying out the process.

The feed composition to zone 5 is adjusted to provide a selectivity enhancing amount of tertiary butanol, generally 1 to 30 wt % and an amount of alkane diluent effective both for heat removal and to reduce isobutylene concentration to a level at which optimum selectivity eg. 97% can be achieved, generally 30 to 80 wt % alkane based on total feed to zone 5.

The alkane diluent used in the dimerization is preferably isobutane or normal butane or mixtures thereof in any proportions and can be added via line 7 as needed. Propane can also be used.

In zone 5, the isobutylene containing feed is contacted with a solid dimerization catalyst, preferably a sulfonic acid resin catalyst such as Amberlyst A-15 of Rohm & Haas, at dimerization reaction conditions whereby exceedingly high reaction selectivity to the dimer is achieved. Generally small amounts of trimer are also formed in zone 5, eg. less than 10% of the converted isobutylene.

The reaction mixture from zone 5 which comprises tertiary butyl alcohol, alkane diluent, unreacted isobutylene as well as isobutylene dimer and trimer, passes via line 8 to separation zone 9 wherein by conventional procedures a stream comprised of unreacted isobutylene, alkane diluent, and tertiary butyl alcohol and small amounts of $C_8$'s is separated and recycled via line 10 to dimerization zone 5. A small purge of this recycle stream may be necessary to maintain tertiary butyl alcohol levels and is provided via line 15. This purge can be recycled to zone 2 to recover the tertiary butyl alcohol, alkane and isobutylene values. A higher boiling stream comprised of alkane together with isobutylene dimer and trimer passes via line 11 to hydrogenation zone 12 wherein the isobutylene polymer products are hydrogenated to polymer gasoline components. Hydrogen is introduced via line 13.

The product stream from zone 12 mainly comprised of isooctane with some isododecane is removed via line 14 as product suitable as a high octane gasoline pool blending component.

The production of tertiary butyl alcohol by means of the Oxirane process is well known and widely practiced on an industrial scale. See, for example, U.S. Pat. No. 3,351,635.

Likewise, the dehydration of tertiary butanol to form isobutylene is well known. See, for example, U.S. Pat. Nos. 5,625,109, 3,510,538, 4,165,343, and 4,155,945.

The dimerization of isobutylene in accordance with the present invention involves various novel features. In the first instance, tertiary butanol is employed as a selectivity enhancing modifier and this results in a substantial improvement in reaction selectivity to the dimer as compared to operation without this modifier.

Secondly, $C_3$–$C_4$ alkane, preferably a butane is employed as a diluent to further enhance reaction selectivity by reducing isobutylene feed concentration, and to aid in removal of the reaction exotherm.

In general, known oligomerization catalysts and conditions can be employed in the oligomerization step. Suitable conditions include temperatures broadly in the range 0 to 200° C., preferably 10 to 100° C., and the use of pressures sufficient to maintain the liquid phase, illustratively above 50 psig, e.g. 50–500 psig.

Known dimerization catalysts can be used including those described in prior art such as U.S. Pat. No. 3,760,026. The use of sulfonic acid type ion exchange resins such as Amberlyst A-15, Dowex 50 and the like is especially preferred.

A feature of the present invention is the use of tertiary butanol as a selectivity enhancing modifier in the olefin dimerization.

The amount of modifying agent which is used is at least 1 wt %, preferably 5 to 15 wt % based on the weight of olefin plus modifying agent plus diluent in the reaction mixture.

By carrying out the oligomerization using both tertiary butyl alcohol and lower alkane, reaction selectivity to diisobutylene of at least 90% based on isobutylene converted is achieved. The remaining reaction product is essentially the trimer, little or no higher polymers are formed.

From oligomerization zone 5, the reaction mixture passes to zone 9 which is appropriately a distillation zone. Unreacted isobutylene, alkane diluent and such tertiary butyl alcohol modifier as remains in the mixture are separated and recycled via line 10 to zone 5. It should be noted that there may be some dehydration of tertiary butyl alcohol in zone 5 and loss of tertiary butyl alcohol in zone 9 which requires the provision of tertiary butyl alcohol via line 4 to the system.

Tertiary butyl alcohol is either consumed or produced in zone 5 according to its equilibrium with isobutylene and water. It is advantageous to operate with the feeds at near-equilibrium conditions such that net tertiary butyl alcohol change is near zero.

The isobutylene polymer product passes via line 11 to hydrogenation zone 12 wherein the unsaturated polymers are hydrogenated in accordance with known procedures to saturated product, mainly isooctane. Hydrogen is introduced via line 12.

Product from zone 12 is removed via line 14 and can be sent directly to a gasoline blending pool as this stream is essentially comprised of high octane gasoline blending hydrocarbons.

The following example illustrates the invention.

Referring to the accompanying drawing, tertiary butanol from an Oxirane propylene oxide/tertiary butanol process forms the feed to the system. This feed comprises about 94 wt % tertiary butanol with the remainder primarily water and acetone.

About 250,000 lbs/hr of the tertiary butanol is fed to dehydration zone 2 via line 1 wherein it is dehydrated at about 371° C. and 200 psig using an alumina dehydration catalyst. Water formed by dehydration and introduced with the feed is removed via line 3 at the rate of 60,000 lbs/hr. A product isobutylene stream comprised by weight of 96.5% isobutylene, 1.0% tertiary butanol, 0.02% water, 1.3% acetone and 1.18% others passes from dehydration zone 2 via line 6 to dimerization zone 5 at the rate of 190,000 lbs/hr. A portion of the Oxirane process tertiary butanol also passes to zone 5 via line 4 at the rate of 20 lbs/hr, (this flow is intermittent as needed), a recycle isobutylene, butane and tertiary butyl alcohol stream from zone 9 comprised by weight of 31.8% isobutylene, 52.3% butane, 5.6% tertiary butyl alcohol and 2.7% $C_8$ and $C_{12}$ isoalkanes passes at the rate of 576,400 lbs/hr via line 10 to zone 5. The butane composition is 10% isobutane and 90% normal butane.

The combined feed streams to zone 5 have a composition by weight of 48% isobutylene, 4.5% tertiary butanol, 44% butane, 0.3% water, 2% higher alkanes and 1.2% others. Zone 5 is a reactor packed with A-15 sulfonic acid resin catalyst and the liquid feed is contacted with the catalyst at 190° C. and 300 psig at a liquid hourly space velocity of 6 $hr^{-1}$.

The reaction mixture is removed from zone 5 via line 8 and passes to separation zone 9 wherein lighter materials are distilled overhead at 60° C. and 50 psig and pass via line 10 to zone 5 as above described. A purge stream in amount of 6650 lbs/hr is removed via line 15.

The bottoms isobutylene dimer mixture comprising by weight 95% diisobutylene, 5% higher isobutylene oligomers, and a trace others passes at the rate of 183350 lbs/hr via line 11 to hydrogenation zone 12 wherein the isobutylene polymers are hydrogenated to isoalkanes. Hydrogen is introduced via line 13 at the rate of 11,500 lbs/hr, a Pd hydrogenation catalyst supported on carbon is used and hydrogenation conditions of 150° C., 200 psig and weight hourly space velocity of 5 $hr^{-1}$ are employed.

The hydrogenation can be carried out in accordance with known procedures using a variety of catalysts and reaction conditions. Although a Pd catalyst is shown above, various other known hydrogenation catalysts can be used. To accommodate the hydrogenation reaction exotherm a cooled recycle is advisable with the rate of recycle to feed about 3:1 by weight.

The hydrogenation reaction product mixture is removed from zone 12 and recovered at the rate of 185,819 lbs/hr via line 14. The excess $H_2$ is recycled to zone 12.

Overall selectivity to isooctane based on tertiary butanol converted in the above system is about 95%. In comparison, where neither the tertiary butanol modifier nor butane diluent is employed, overall selectivity is only about 30%.

We claim:

1. In a process for the selective oligomerization of isobutylene to the diner, the improvement which comprises oligomerizing the isobutylene in the presence of $C_3$–$C_4$ alkane diluent in amount sufficient to enhance oligomerization selectivity to the dimer and to absorb the reaction exotherm, and tertiary butanol in amount sufficient to promote oligomerization selectivity to the dimer.

2. A process for the production of a high-octane gasoline blending mixture mainly comprised of isooctane which comprises oligomerizing isobutylene to the dimer in at least 90% selectivity, the oligomerization being carried out with a sulfonic acid resin catalyst, tertiary butanol selectivity enhancing modifier and $C_4$ alkane diluent, and hydrogenating oligomerization products to form mainly isooctane.

3. The process of claim 1 wherein the isobutylene is formed by dehydration of tertiary butanol.

* * * * *